(12) United States Patent
Marseille et al.

(10) Patent No.: US 9,302,035 B2
(45) Date of Patent: Apr. 5, 2016

(54) IMPLANTABLE BLOOD FLOW SYSTEM WITH SECURE REMOTE CONTROL

(71) Applicant: CircuLite, Inc., Teaneck, NJ (US)

(72) Inventors: Oliver Marseille, Aachen (DE); Kirk A. Lehmann, Aachen (DE); Tobias Schleicher, Eschweiler (DE); J. Christopher Flaherty, Auburndale, FL (US)

(73) Assignee: CircuLite, Inc., Teaneck, NJ (US)

( * ) Notice: Subject to any disclaimer, the term of this patent is extended or adjusted under 35 U.S.C. 154(b) by 0 days.

(21) Appl. No.: 14/449,423

(22) Filed: Aug. 1, 2014

(65) Prior Publication Data
US 2015/0038771 A1   Feb. 5, 2015

Related U.S. Application Data

(60) Provisional application No. 61/861,704, filed on Aug. 2, 2013.

(51) Int. Cl.
*A61M 1/12* (2006.01)
*A61M 1/10* (2006.01)
*G06F 19/00* (2011.01)

(52) U.S. Cl.
CPC ............ *A61M 1/1086* (2013.01); *A61M 1/122* (2014.02); *G06F 19/3406* (2013.01); *G06F 19/3418* (2013.01)

(58) Field of Classification Search
None
See application file for complete search history.

(56) References Cited

U.S. PATENT DOCUMENTS

| | | | |
|---|---|---|---|
| 4,662,358 A | 5/1987 | Farrar et al. |
| 4,688,998 A | 8/1987 | Olsen et al. |
| 5,267,940 A | 12/1993 | Moulder |
| 5,352,180 A | 10/1994 | Candelon et al. |
| 5,676,162 A | 10/1997 | Larson, Jr. et al. |
| 5,820,542 A | 10/1998 | Dobak, III et al. |

(Continued)

FOREIGN PATENT DOCUMENTS

| | | |
|---|---|---|
| WO | 2012078873 A1 | 6/2012 |
| WO | 2014107424 A2 | 7/2014 |

OTHER PUBLICATIONS

European Patent Office, International Search Report and Written Opinion in PCT Application Serial No. PCT/US14/049393, Oct. 31, 2014.

(Continued)

*Primary Examiner* — Kennedy Schaetzle
(74) *Attorney, Agent, or Firm* — Wood, Herron & Evans, LLP (57) ABSTRACT

A fluid flow system for a patient comprises a controller and an implantable pump assembly. The controller comprises a processing unit and a battery. The processing unit includes a signal generator and one or more pump operational parameters. The signal generator provides a drive signal. The battery provides power to the processing unit. The implantable pump assembly receives the drive signal from the processing unit and propels fluid based on the drive signal. The system includes a local communication device and a remote communication device that each include a unique identifier produced by a security key generator. The remote communication device includes a code generator that produces encrypted commands. The local communication device receives the encrypted commands and modifies a pump operational parameter of the processing unit based on the received encrypted command.

30 Claims, 4 Drawing Sheets

(56) References Cited

U.S. PATENT DOCUMENTS

| | | | |
|---|---|---|---|
| 5,888,242 | A | 3/1999 | Antaki et al. |
| 6,066,086 | A | 5/2000 | Antaki et al. |
| 6,116,862 | A | 9/2000 | Rau et al. |
| 6,176,848 | B1 | 1/2001 | Rau et al. |
| 6,387,323 | B1 | 5/2002 | Afzal et al. |
| 6,527,699 | B1 | 3/2003 | Goldowsky |
| 6,540,658 | B1 | 4/2003 | Fasciano et al. |
| 6,610,004 | B2 | 8/2003 | Viole et al. |
| 6,783,328 | B2 | 8/2004 | Lucke et al. |
| 6,991,595 | B2 | 1/2006 | Burke et al. |
| 7,039,810 | B1 | 5/2006 | Nichols |
| 7,591,777 | B2 | 9/2009 | LaRose |
| 7,645,225 | B2 | 1/2010 | Medvedev et al. |
| 7,742,821 | B1 | 6/2010 | Vamos et al. |
| 7,850,594 | B2 | 12/2010 | Sutton et al. |
| 7,862,501 | B2 | 1/2011 | Woodard |
| 7,963,905 | B2 | 6/2011 | Salmonsen et al. |
| 7,988,728 | B2 | 8/2011 | Ayre |
| 8,096,935 | B2 | 1/2012 | Sutton et al. |
| 8,226,712 | B1 | 7/2012 | Frazier et al. |
| 2003/0060765 | A1 * | 3/2003 | Campbell et al. ............. 604/131 |
| 2003/0074144 | A1 | 4/2003 | Freed et al. |
| 2005/0215843 | A1 | 9/2005 | Medvedev |
| 2006/0074465 | A1 | 4/2006 | Webb |
| 2007/0132597 | A1 * | 6/2007 | Rodgers ...................... 340/573.1 |
| 2007/0276480 | A1 | 11/2007 | Tansley et al. |
| 2009/0138080 | A1 | 5/2009 | Siess et al. |
| 2009/0226328 | A1 * | 9/2009 | Morello ............................ 417/1 |
| 2010/0168848 | A1 | 7/2010 | Horvath et al. |
| 2010/0274218 | A1 * | 10/2010 | Yodfat et al. .................. 604/504 |
| 2011/0015693 | A1 | 1/2011 | Williamson |
| 2012/0078030 | A1 | 3/2012 | Bourque |
| 2012/0150291 | A1 | 6/2012 | Aber et al. |
| 2012/0172657 | A1 | 7/2012 | Marseille et al. |
| 2014/0073837 | A1 | 3/2014 | Kerkhoffs et al. |
| 2014/0276557 | A1 * | 9/2014 | Vaishya ....................... 604/505 |

OTHER PUBLICATIONS

European Patent Office, Second Written Opinion in PCT Application Serial No. PCT/US14/049393, Jul. 15, 2015.

European Patent Office, International Preliminary Report on Patentability in PCT Application Serial No. PCT/US14/049393, Oct. 1, 2015.

* cited by examiner

IMPLANTABLE BLOOD FLOW SYSTEM WITH SECURE REMOTE CONTROL

RELATED APPLICATIONS

This application claims the priority of U.S. Provisional Application Ser. No. 61/861,704, filed Aug. 2, 2013, the disclosure of which is hereby incorporated by reference herein.

This application is also related to U.S. Provisional Patent Ser. No. 61/700,518, entitled "BLOOD FLOW SYSTEM WITH VARIABLE SPEED CONTROL", filed Sep. 13, 2012, the contents of which is incorporated herein by reference in its entirety.

TECHNICAL FIELD

The present invention relates generally to medical devices, systems and methods, and more particularly, to devices and methods for assisting in the conduction of bodily fluids such as blood.

BACKGROUND

Various devices, systems and methods have been utilized to assist in conducting bodily fluids. For instance, blood pumps with inflow and outflow grafts assist the heart in circulating blood in a patient experiencing congestive heart failure, and a transplant organ has either not been located or the patient is not a suitable candidate for the transplant. Accordingly, the blood pump can be fluidically attached to the left side of the heart and then located remotely, such as subcutaneously or submuscularly in a manner similar to a pacemaker, in what is referred to as a "pump pocket." The pump pocket can be generally located at a position that is accessible by a surgical incision from below the collarbone, over the pectoral muscle, and toward the breast. A cannula can then be used to fluidically couple the heart to the pump. In still another example, a cannula is inserted into the bladder or kidney, such as in dialysis or to treat urinary obstruction or infection.

A fluid drive module, such as a pump, can be used to circulate the bodily fluid. Areas of insufficient flow, such as low-flow areas within or proximate to the fluid drive module, can result in the circulated fluid undesirably transitioning to solid matter. With blood pumping systems, blood in a stasis or near-stasis condition can transition to thrombus. Creation of thrombus or other solid matter can result in reduced flow of the fluid drive module or, more significantly, release of solid matter into the patient such as a released embolus that causes a stroke, heart attack, or other ischemic event. Blood pump implantation procedures include making precise measurements to properly size (e.g. cut to length) flow conduits and require specific order of flow conduit attachments (e.g. order of attachment to body lumens).

Implanted blood pumps and other adjustable implanted devices often require control via a device external to the patient, such as a device that may reside or otherwise be present at the patient location from time to time. There is a need for safeguarded systems that prevent unacceptable or otherwise unauthorized changes to one or more operational parameters of the implanted device.

SUMMARY

According to an aspect of the invention, a fluid flow system for a patient comprises a controller, an implantable pump assembly and a security key generator. The controller comprises a processing unit and a battery. The processing unit comprises a signal generator and one or more pump operational parameters, and is constructed and arranged to deliver a drive signal. The battery is constructed and arranged to provide power to the processing unit. The implantable pump assembly is constructed and arranged to receive the drive signal from the processing unit and propel fluid based on the drive signal. The security key generator is constructed and arranged to produce a unique identifier. The system can include a remote communication device comprising a code generator and the unique identifier produced by the security key generator. The code generator can be constructed and arranged to produce an encrypted command based on the unique identifier. The system can include a local communication device comprising the unique identifier. The local communication device can be constructed and arranged to receive the encrypted commands from the remote communication device and modify a pump operational parameter of the processing unit based on the received encrypted command.

In some embodiments, the implantable pump assembly is constructed and arranged to propel blood, such as to propel blood from a heart chamber to a blood vessel.

In some embodiments, the processing unit is constructed and arranged to deliver the drive signal to the implantable pump assembly based on the one or more pump operational parameters.

In some embodiments, the system further comprises a programmer including a first connector, wherein the processing unit includes a second connector constructed and arranged to operably connect to the first connector, wherein the programmer communicates with the processing unit via the first connector. The second connector can be constructed and arranged to removably connect to the first connector. The second connector can be constructed and arranged to operably connect to the first connector with a connection type selected from the group consisting of: electrical connection; optical connection; and combinations thereof. The programmer can be constructed and arranged to be maintained at a location remote from the patient. The programmer can be constructed and arranged to modify at least one pump operational parameter of the processing unit. The programmer can be constructed and arranged to prevent the patient from changing the at least one pump operational parameter. The programmer can be constructed and arranged to attach to wall power. The programmer can be constructed and arranged to transfer power to the controller.

In some embodiments, the processing unit comprises a wireless transmitter. The processing unit can comprise data and the wireless transmitter can be constructed and arranged to transmit the data to a separate device. The system can further comprise a wireless receiver constructed and arranged to receive data from the processing unit wireless transmitter. The wireless receiver can be constructed and arranged to transmit data to a communication network. The communication network can comprise a network selected from the group consisting of: internet; cellular service; satellite communication; fiber optic network; phone line; and combinations thereof.

In some embodiments, the one or more pump operational parameters comprise a parameter selected from the group consisting of: pump flow rate; pump maximum flow rate; pump minimum flow rate; pump fluid drive element speed; pump maximum fluid drive element speed; pump minimum fluid drive element speed; speed alternations and/or waveforms; alarm status; alarm level; alarm sensitivity; alarm type; temperature level; battery status; and combinations thereof.

In some embodiments, the one or more pump operational parameters comprise a pump flow rate parameter.

In some embodiments, the one or more pump operational parameters comprise a pump rotational speed parameter. The implantable pump assembly can comprise a rotatable fluid drive element and the pump rotational speed parameter can comprise the rotational speed of the fluid drive element.

In some embodiments, the one or more pump operational parameters comprise an alarm parameter. The alarm parameter can comprise a parameter correlating to a pump status selected from the group consisting of: low flow condition; high flow condition; low battery condition; air and/or other gas detected condition; battery disconnected condition; undesired pump stoppage; temperature out of acceptable range; motor current above a maximum threshold; motor current below a minimum threshold; undesired supply current status; undesired supply current fluctuation level; and combinations thereof.

In some embodiments, the one or more pump operational parameters comprise a first set of alarm states that are resettable by an encrypted command and a second set of alarm states that are not resettable by an encrypted command. The second set of alarm states can comprise an alarm caused by a pump status selected from the group consisting of: undesired pump stoppage; temperature out of acceptable range; motor current above a maximum threshold; motor current below a minimum threshold; and combinations thereof.

In some embodiments, the one or more pump operational parameters comprise an alarm state parameter. The processing unit can be constructed and arranged to reset an alarm based on a change to the alarm state parameter.

In some embodiments, the processing unit comprises an alarm algorithm, and the one or more pump operational parameters comprise an alarm algorithm parameter. The alarm algorithm can be constructed and arranged to compare a value to a threshold value and the algorithm parameter comprises the threshold value. The alarm algorithm can comprise an adjustable sensitivity and the alarm algorithm parameter determines the sensitivity. The one or more pump operational parameters can comprise a first set of alarm states that are resettable by an encrypted command, and wherein the alarm algorithm is constructed and arranged to limit the number of times the one or more pump operational parameters can be reset. The system can further comprise a reset counter and a pump operational parameter comprising a reset threshold, wherein the threshold is adjustable. The threshold can be adjustable by the manufacturer of the system.

In some embodiments, the battery is constructed and arranged to removably attach to the processing unit.

In some embodiments, the battery comprises a rechargeable battery.

In some embodiments, the controller comprises a second battery constructed and arranged to provide power to the processing unit.

In some embodiments, the security key generator is further constructed and arranged to produce a second unique identifier for a second fluid flow system.

In some embodiments, the system further comprises a second local communication device and wherein the security key generator is further constructed and arranged to produce a second unique identifier for the second local communication device. The remote communication device can further comprise the second unique identifier.

In some embodiments, the system further comprises a second remote communication device and wherein the security key generator is further constructed and arranged to produce a second unique identifier for the second remote communication device. The local communication device can further comprise the second unique identifier.

In some embodiments, the security key generator comprises a random code generator constructed and arranged to produce the unique ID.

In some embodiments, the remote communication device comprises a first read-protected memory module and the local communication device comprises a second read-protected memory module and the unique identifier is stored in the first read-protected memory module and the second read-protected memory module.

In some embodiments, the remote communication device is constructed and arranged to be maintained at a location remote from the patient.

In some embodiments, the remote communication device is constructed and arranged to send the encrypted commands to the local communication device via a communication network. The communication network can comprise a network selected from the group consisting of: internet; cellular service; satellite communication; fiber optic network; phone line; and combinations thereof.

In some embodiments, the remote communication device is constructed and arranged to send encrypted commands using at least one of a 64 bit encryption algorithm or a 256 bit encryption algorithm.

In some embodiments, the remote communication device is constructed and arranged to send the encrypted commands to the local communication device via a first human operator. The first human operator can receive the encrypted commands from a second human operator. The first human operator can receive the encrypted commands from a communication network, such as a communication network selected from the group consisting of: the internet; cellular service; satellite communication; fiber optic network; phone line; and combinations thereof.

In some embodiments, the code generator is constructed and arranged to produce the encrypted commands using a cryptographic secure hash function.

In some embodiments, the code generator is constructed and arranged to produce a first encrypted command by encrypting pump operational parameter change information with the unique identifier. The remote communication device can comprise a user interface constructed and arranged to allow an operator to input the pump operational parameter change information. The first encrypted command can comprise a command received by the local communication device. The local communication device can be constructed and arranged to decrypt the first encrypted command and transmit the pump operational parameter change information to the processing unit if the first encrypted command is based on a proper unique identifier. The local communication device can be constructed and arranged to decrypt the first encrypted command and not transmit the pump operational parameter change information to the processing unit if the first encrypted command is not based on a proper unique identifier. The local communication device can comprise a status indicator constructed and arranged to confirm the acceptability of the first encrypted command. The local communication device can be constructed and arranged to be attached to the processing unit if the acceptability of the first encrypted command is confirmed. The status indicator can comprise an indicator selected from the group consisting of: light emitting element; vibrational transducer; audio transducer; alphanumeric display; and combinations thereof.

In some embodiments, the local communication device is constructed and arranged to produce data and wherein the remote communication device is constructed and arranged to upload the data from the local communication device. The local communication device can comprise a diagnostic algorithm and the data can comprise diagnostic data produced by the diagnostic algorithm. The data can be uploaded prior to modifying a pump operational parameter.

In some embodiments, the remote communication device is constructed and arranged to communicate with a single local communication device.

In some embodiments, the local communication device comprises a first local communication device, wherein the system further comprises a second local communication device comprising a second unique identifier produced by the security key generator, wherein the remote communication device further comprises the second unique identifier, and wherein the remote communication device is constructed and arranged to communicate with the first local communication device and the second local communication device. The remote communication device can comprise a lookup table comprising the first unique identifier and the second unique identifier.

In some embodiments, the system further comprises one or more sensors selected from the group consisting of: flow sensor; magnetic sensor; electrical current sensor; rotational sensor; a voltage sensor; a current sensor; a position sensor; and combinations of thereof. The one or more sensors can be positioned in the controller and/or the implantable pump assembly.

In some embodiments, the encrypted commands comprise at least one verification bit. The at least one verification bit can comprise a checksum.

In some embodiments, the encrypted commands comprise temporal information. The temporal information can comprise temporal information selected from the group consisting of: time of day information; date information; and combinations thereof. The local communication device can be constructed and arranged to confirm the applicability of the temporal information.

In some embodiments, the system is constructed and arranged to prevent multiple uses of any encrypted command. The system can be constructed and arranged to prevent the multiple uses based on temporal information included in the encrypted commands.

In some embodiments, the local communication device is constructed and arranged to be maintained at a location proximate to the patient.

In some embodiments, the local communication device comprises a receiver constructed and arranged to receive the encrypted commands from the remote communication device over a communication network. The communication network can comprise a network selected from the group consisting of: internet; cellular service; satellite communication; fiber optic network; phone line; and combinations thereof. The local communication device can comprise a first hardware module comprising the receiver and a second hardware module comprising a decryption algorithm constructed and arranged to decode the encrypted commands. The first hardware module and the second hardware module can be constructed and arranged to prevent access to the decryption algorithm via the communication network. The first hardware module and the second hardware module can be constructed and arranged to prevent transmission of any signal received from the communication network other than through the decryption algorithm.

In some embodiments, the local communication device further comprises a user interface constructed and arranged to receive the encrypted commands from a first human operator. The user interface can comprise a data input module. The data input module can comprise a keyboard. The data input module can comprise a voice recognition module. The first human operator can receive the encrypted commands from a second human operator.

In some embodiments, the local communication device is constructed and arranged to receive a message and to alert a user if the message is determined to be invalid. The local communication device is constructed and arranged to enter an alert state if multiple invalid messages are received. The local communication device can be constructed and arranged to enter alarm state if the multiple invalid messages are received within a pre-determined time period. The local communication device can be constructed and arranged to enter alarm state if the number of invalid messages received surpasses a threshold.

In some embodiments, the local communication device is constructed and arranged to communicate with a single remote communication device.

In some embodiments, the remote communication device comprises a first remote communication device, wherein the system further comprises a second remote communication device comprising a second unique identifier produced by the security key generator, wherein the local communication device further comprises the second unique identifier, and wherein the local communication device is constructed and arranged to communicate with the first remote communication device and the second remote communication device. The local communication device comprises a lookup table comprising the first unique identifier and the second unique identifier.

In some embodiments, wherein the system further comprises an error correction algorithm constructed and arranged to correct errors in communication between the local communication device and the remote communication device. The remote communication device can comprise the error correction algorithm. The local communication device can comprise the error correction algorithm.

According to another aspect of the present inventive concepts, a method of modifying an operational parameter of a fluid flow system comprises providing a fluid flow system comprising a controller, an implantable pump assembly and a security key generator. The controller comprises a processing unit and a battery. The processing unit comprises a signal generator and one or more pump operational parameters, and is constructed and arranged to deliver a drive signal. The battery is constructed and arranged to provide power to the processing unit. The implantable pump assembly is constructed and arranged to receive the drive signal from the processing unit and propel fluid based on the drive signal. The security key generator is constructed and arranged to produce a unique identifier. The fluid flow system can further include a remote communication device comprising a code generator and the unique identifier produced by the security key generator. The code generator can be constructed and arranged to produce an encrypted command based on the unique identifier. The fluid flow system can include a local communication device comprising the unique identifier. The local communication device can be constructed and arranged to receive the encrypted commands from the remote communication device and modify a pump operational parameter of the processing unit based on the received encrypted command. The method can further comprise having the security key generator produce the unique identifier; incorporating the unique identifier into the remote communication device and the local communication device; receiving the encrypted command with the local communication device and confirming the acceptability of the encrypted command; and/or modifying the one or more pump operational parameters of the processing unit if the encrypted command acceptability is confirmed.

In some embodiments, the fluid flow system comprises a fluid flow system as described hereabove.

In some embodiments, modifying the one or more pump operational parameters modifies a pump alarm state.

In some embodiments, modifying the one or more pump operational parameters modifies a pump flow rate.

The technology described herein, along with the attributes and attendant advantages thereof, will best be appreciated and understood in view of the following detailed description taken in conjunction with the accompanying drawings in which representative embodiments are described by way of example.

BRIEF DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

DETAILED DESCRIPTION OF THE DRAWINGS

Reference will now be made in detail to the present embodiments of the technology, examples of which are illustrated in the accompanying drawings. The same reference numbers are used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Figure 1:
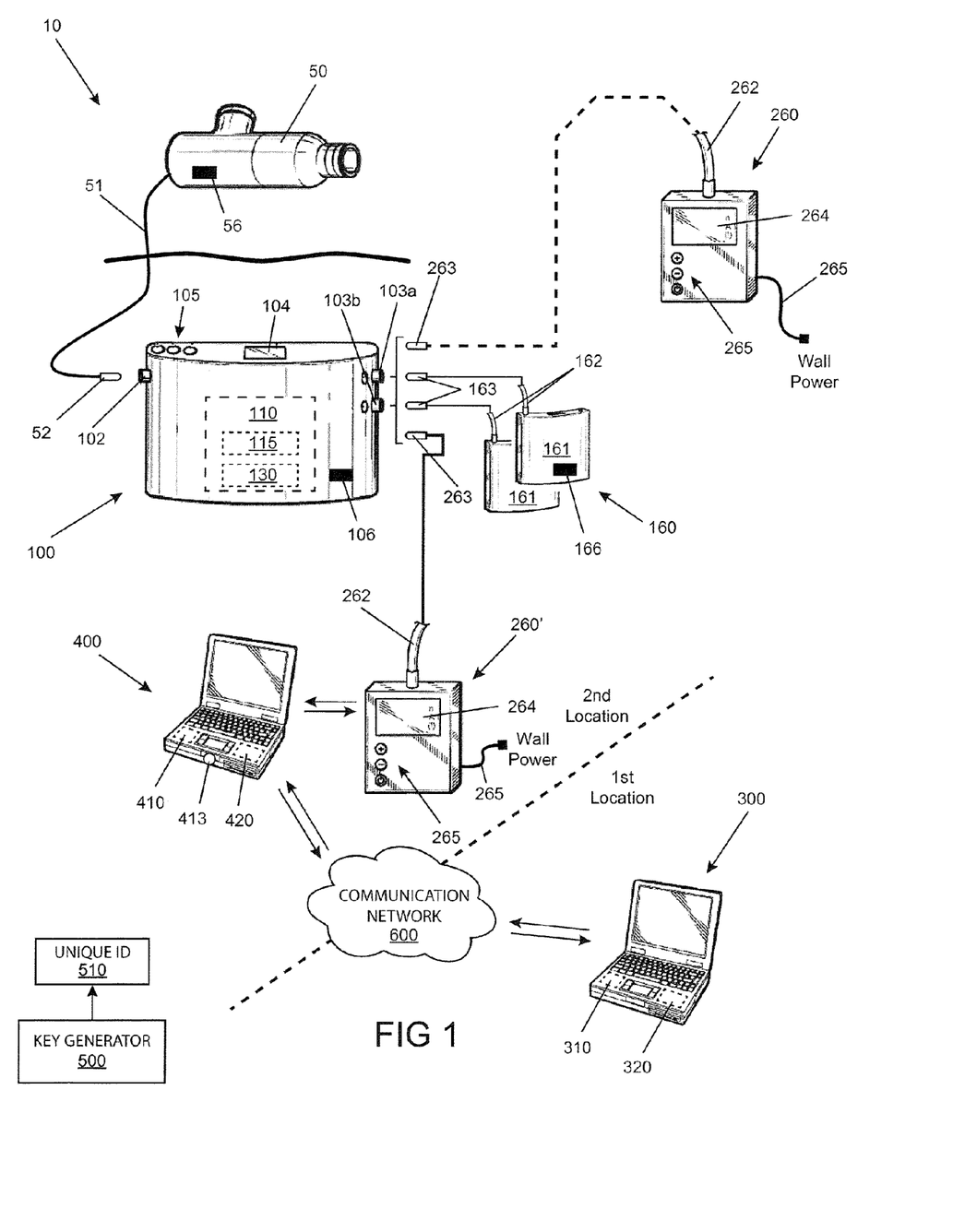
FIG. 1 is a schematic view of a fluid flow system including one or more components configured to be remotely accessed, consistent with the present inventive concepts.

Referring now to FIG. 1, a schematic view of a fluid flow system for a patient is illustrated, including one or more components configured to be remotely accessed, consistent with the present inventive concepts. System 10, typically a blood flow system, includes pump 50 and controller 100. Pump 50 can be configured to assist in blood flow within the circulatory system of a patient, such as when pump 50 is constructed and arranged to propel blood from a heart chamber to a blood vessel. In some embodiments pump 50 comprises a rotational drive assembly similar to that described in U.S. Pat. No. 6,116,862, entitled "Blood Pump", and/or a rotational drive assembly similar to that described in U.S. Pat. No. 6,176,848, entitled "Intravascular Blood Pump", the contents of which are each incorporated herein by reference in their entirety. System 10 includes a remote communication device 300 and a local communication device 400. Communication device 300 and communication device 400 are configured to send and/or receive information to and/or from each other via a communication network 600. In some embodiments, Communication network 600 can comprise a network selected from the group consisting of: internet; cellular service; satellite communication; fiber optic network; phone line; and combinations of these. Local communication device 400 is configured to receive encrypted commands from remote communication device 300, and locally decode and transfer acceptable commands to controller 100. Remote communication device 300 is configured to be maintained at a first location, remote from the patient, such as a physician's office, hospital, or other clinical setting, and local communication device 400 is configured to be maintained at a second location, local to the patient, such as at the patients residence or patient care location.

A rotational drive assembly of pump 50, or other fluid propulsion assembly within pump 50, is configured to operate based on parameters received from controller 100, via a drive signal. Pump 50 can include a wire or wire bundle, conduit 51, which includes connector 52 at one end. Conduit 51 can comprise one or more wires, optical fibers, and the like configured to operably connect pump 50 to controller 100, such as to carry one or more drive signals (e.g. a signal based on pump operational parameters) and/or power from controller 100 to pump 50. Conduit 51 can also be configured to carry data from pump 50 to controller 100, such as pump or patient diagnostic data or alarm state data. Conduit 50 can be configured to be at least partially inserted into a patient, such as a transcutaneous insertion used to connect an implanted pump 50 to controller 100. In some embodiments, signals and/or power between pump 50 and controller 100 may be transmitted wirelessly, such as via inductive coupling, electromagnetic waves, or other wireless communication.

Pump 50 can include one or more sensors 56, such as one or more sensor selected from the group consisting of: flow sensor; magnetic sensor; electrical current sensor; rotational sensor; and combinations of these. In some embodiments, controller 100 and/or pump 50 can comprise a Bluetooth transceiver, not shown but configured to send and/or receive data, such as diagnostic data collected from one or more sensors 56 of pump 50.

Controller 100 comprises a processing unit, processor 110, and a signal generating unit, signal generator 115. Controller 100 can further include multiple access ports, such as ports 102, 103a and 103b. Controller 100 can include a user interface, such as a user interface including display 104 and/or buttons 105. In some embodiments, display 104 comprises a touch screen display. Controller 100 can include one or more sensors 106, such as one or more sensors selected from the group consisting of: a voltage sensor; a current sensor; a position sensor; and combinations of these. Port 102 attaches to connector 52, operably connecting processor 110 to pump 50. Signal generator 115 is configured to generate a drive signal, which can be transmitted to pump 50 via conduit 51. The drive signal can be generated based on one or more pump operational parameters, such as one or more pump operational parameters selected from the group consisting of: pump flow rate; pump maximum flow rate; pump minimum flow rate; pump fluid drive element speed; pump maximum fluid drive element speed; pump minimum fluid drive element speed; speed alternations and/or waveforms; alarm status; alarm level; alarm sensitivity; alarm type; temperature level; battery status; and combinations of these. Processor 110 can be configured to alter these pump operational parameters based on commands received from one or more programming devices, such as are described herein. Controller 100 can further comprise a wireless communication assembly, transceiver 130. Transceiver 130 can be configured to wirelessly transmit pump operational parameter to pump 50 and/or may wirelessly communicate with an external component, such as a smart phone or other handheld device, to relay diagnostic or other operational data. Transceiver 130 can be configured as a Bluetooth transceiver.

System 10 also includes one or more power supply components, such as power modules 160. As shown, each power module 160 comprises a battery 161, a conduit 162 and a connector 163. Conduit 162 can comprise one or more wires, optical fibers, and the like and include connector 163 at one end. Connector 163 is configured to operably attach a power module 160 to controller 100 at ports 103a or 103b. In some embodiments, a power module 160 comprises one or more sensors 166, such as one or more voltage, current or power sensors which provide a signal to controller 100 via conduit 162. In some embodiments, controller 100 is configured to operate using two power modules 160 connected to port 103a and/or 103b, such that controller 100 operates without interruption (e.g. without power failure) when power module 160 is disconnected. Power modules 160 can comprise rechargeable batteries. In these embodiments, power modules 160 can be configured to support a predetermined number of charge cycles and/or can provide a self-diagnostic indicator such that a "bad" power module 160 can be disposed of and replaced. Power modules 160 may be disconnected from controller 100 such as while replacing a depleted power module 160 with a fully charged power module 160, or during a programming procedure, such as when a programmer is connected to controller 100 via port 103a or 103b, as is described herebelow. Controller 100 can also include an internal power supply (not shown but such as a battery or capacitor) such that all external batteries 160 may be removed for a short period without operational interruption.

System 10 can be configured to enter into one or more alarm states, such as an alarm state triggered by a detected, undesired condition of pump 50. A pump operational parameter can comprise an alarm state associated with an undesired pump status. In some embodiments, an alarm state correlates to a pump status selected from the group consisting of: low flow condition; high flow condition; low battery condition; air and/or other gas detected condition; battery disconnected condition; undesired pump stoppage; temperature out of acceptable range; motor current above a maximum threshold; motor current below a minimum threshold; undesired supply current status; undesired supply current fluctuation level; and combinations of these. In some embodiments, a pump operational parameter of system 10 comprises one or more thresholds used to trigger an alarm state of system 10. Threshold-based pump operational parameters can be set and/or modified via an encrypted command received from a remote location (e.g. sent by remote communication device 300 over communication network 600). In some embodiments, a pump operational parameter of system 10 comprises an alarm status, such as an on or off status signifying whether system 10 is currently in an alarm state. In these embodiments, the alarm status may require a reset such as a reset that can be performed via an encrypted command from a remote location. System 10 can be configured to have one or more alarm states that are resettable (e.g. to allow continued pump use) and one or more alarm states that are not resettable (e.g. continued pump use is prevented or otherwise requires additional steps to reactivate pumping). In some embodiments, a non-resettable alarm state can be associated with a life-threatening alarm condition requiring on-site attention, such as a pump status selected from the group consisting of: undesired pump stoppage; temperature out of acceptable range; motor current above a maximum threshold; motor current below a minimum threshold; and combinations of these. In some embodiments, a threshold parameter can be modified after an alarm state is reached, such as a low-flow threshold that is reduced after a particular low-flow alarm condition occurs. Processing unit 110 and/or another component of system 10 can comprise an alarm algorithm that uses one or more alarm algorithm parameters, such as a threshold as described above or a variable used to determine sensitivity of the algorithm. In some embodiments, one or more pump operational parameters comprise a set of multiple alarm states (e.g. a single alarm state or multiple alarm states) that can be reset as described hereabove. In these embodiments, the system may include an algorithm configured to prevent excessive resetting of the alarm state, such as to force the system to be analyzed for defects by the manufacturer or other technical service. Prevention of excessive resetting can be accomplished with the use of an alarm reset counter which increments after each reset is performed. After each reset, the output of the counter is compared to an alarm algorithm parameter comprising a maximum reset threshold value. After the threshold is achieved, subsequent resets for one or more alarm states is prevented. In some embodiments, the threshold value is adjustable, such as an adjustment performed only by the manufacturer.

System 10 includes one or more programming devices, such as programmer 260 and/or programmer 260' as shown. In some embodiments, programmer 260 is configured to be a physician-operated programmer and programmer 260' is configured to be a patient-operated programmer. In some embodiments, a clinician-operated programmer 260 can be configured to set or modify all or a majority of pump operational parameters, while a patient-operated programmer 260' can be configured set or modify a more limited number of pump operational parameters. For example, a patient operated programmer 260' can be prevented from setting or modifying any pump operational parameters (e.g. programmer 260' is prevented from setting or modifying any pump operational parameters unless a clinician or other authorization code is provided), such as via local communication device 400. In some embodiments, programmer 260' is configured to relay commands received from remote communication device 300 to controller 100. In some embodiments, programmer 260 and programmer 260' can comprise a single controller configured to operate in both a physician-mode and a patient-mode. In these embodiments, the patient-mode can be configured to have limited ability to set or modify any pump operational parameters, while the clinician-mode may be configured to set of modify all or a majority of pump operational parameters, as described above. Undesired or inadvertent transitioning between patient-mode and clinician-mode can be accomplished with a username and/or password. In some embodiments, a physician-operated programmer 260 can be configured to be maintained at a physician's office, and can be used to modify pump operational parameters during an initial and/or subsequent patient visits to the physician's office.

Programmer 260 and/or 260' (generally 260) each comprise a conduit 262 including one or more wires, optical fibers and the like with a connector 263 at one end. Programmer 260 further comprises a user interface including display 264 and buttons 265. In some embodiments, display 265 comprises a touch screen display. Programmer 260 is configured to be operably connected to controller 100 via ports 103a and/or 103b, and download pump operational parameters to processor 110. In some embodiments, ports 103a and/or 103b can provide a connection selected from the group consisting of: an electrical connection; an optical connection; and combinations of these. In some embodiments, programmer 260 can comprise a wireless transceiver, such as a Bluetooth transceiver, configured to wirelessly transmit pump operational parameters to processor 110, such as via transceiver 130. In a physician-mode as described hereabove, display 264 and/or buttons 265 can be configured to receive the input of pump operational parameters into programmer 260 from the clinician or other authorized caregiver, for upload to controller 100. Display 264 can display details of the pump operational parameters to be uploaded, and can also display the status of an upload process (e.g. the percent complete of an upload, or indication of a successful upload). Display 264 and/or buttons 265 can be further configured to initiate the upload of parameters to programmer 260, such as from local communication device 400. Display 264 and/or buttons 265 can be configured to initiate the download of one or more parameters to controller 100 from programmer 260.

Remote communication device 300 and local communication device 400 each comprise a unique ID 510. System 10 includes a unique ID generator, key generator 500. Key generator 500 can comprise a random code generator and can be used in manufacturing to randomly generate unique ID 510, which is configured to be embedded within devices 300 and 400, linking remote communication device 300 and local communication device 400. Key generator 500 can be configured to provide multiple unique ID's 510, such as to provide a unique ID for a second system 10 (i.e. a second set of communication devices for providing remote access for a second implantable pump assembly for a second patient). Embedded unique ID 510 ensures that encoded commands sent from device 300 can only be properly decoded by device 400 (i.e. any given remote communication device 300 only works with its corresponding local communication device 400), as is described herebelow in reference to FIGS. 3A and 3B. Other system components can also comprise unique ID 510 (e.g. controller 100 or power modules 160) such as to ensure that each uniquely identified component can only operate with components of a particular system 10 with matching unique ID 510.

Remote communication device 300 includes a code generation algorithm and associated electronics, code generator 310, configured to produce encrypted commands, based on unique ID 510. In some embodiments, the encrypted commands are created using 64 bit encryption algorithm, or 256 bit encryption algorithm. Remote communication device further includes a communications module, transceiver 320, configured to transmit the encrypted command via communication network 600, to local communication device 400. Local communication device 400 includes a communication module, transceiver 420, configured to receive the encrypted command from remote communication device 300. Local communication device includes a decoding algorithm and associated electronics, decoder 410, configured to decode encrypted commands received from remote communication device 300, based on unique ID 510. Local communication device 400 is configured to modify the pump operational parameters of processor 110 based on the encrypted command, such as by decrypting the command, confirming validity of the command, and sending the operational parameters to controller 100 via programmer 260'. Local communication device 400 can determine the validity of a received command using a decryption algorithm based on unique ID 510 or as is otherwise described in reference to decoder 410 of FIG. 3B herebelow. Local communication device 400 can further include a port 413, such as to operably connect to programmer 260' via connector 263. Devices 300 and 400 are further described in reference to FIGS. 3A and 3B herebelow.

In some embodiments, local communication device 400 can include one or more algorithms configured to produce data, such as a diagnostic algorithm configured to run a system or component test to produce diagnostic data. Remote communication device 300 can be configured to upload data from local communication device 400, such as an upload triggered by a secure upload command based on the unique identifier 510. Uploaded data can include the diagnostic data described hereabove, such as diagnostic data which is reviewed prior to changing one or more pump operational parameters.

In some embodiments, remote communication device 300 and/or local communication device 400 include an error correction algorithm, such as an algorithm constructed and arranged to correct errors in data transmission or other communications.

In some embodiments, one or more programmers 260 can be attached to a source of power, such as when programmers 260 include an electrical conduit 262 (e.g. an attachable wire pair or power supply) configured to operably connect to a standard AC wall outlet as shown. In these embodiments, one or more programmers 260 can transfer power received from the wall outlet to controller 100.

Figure 2:
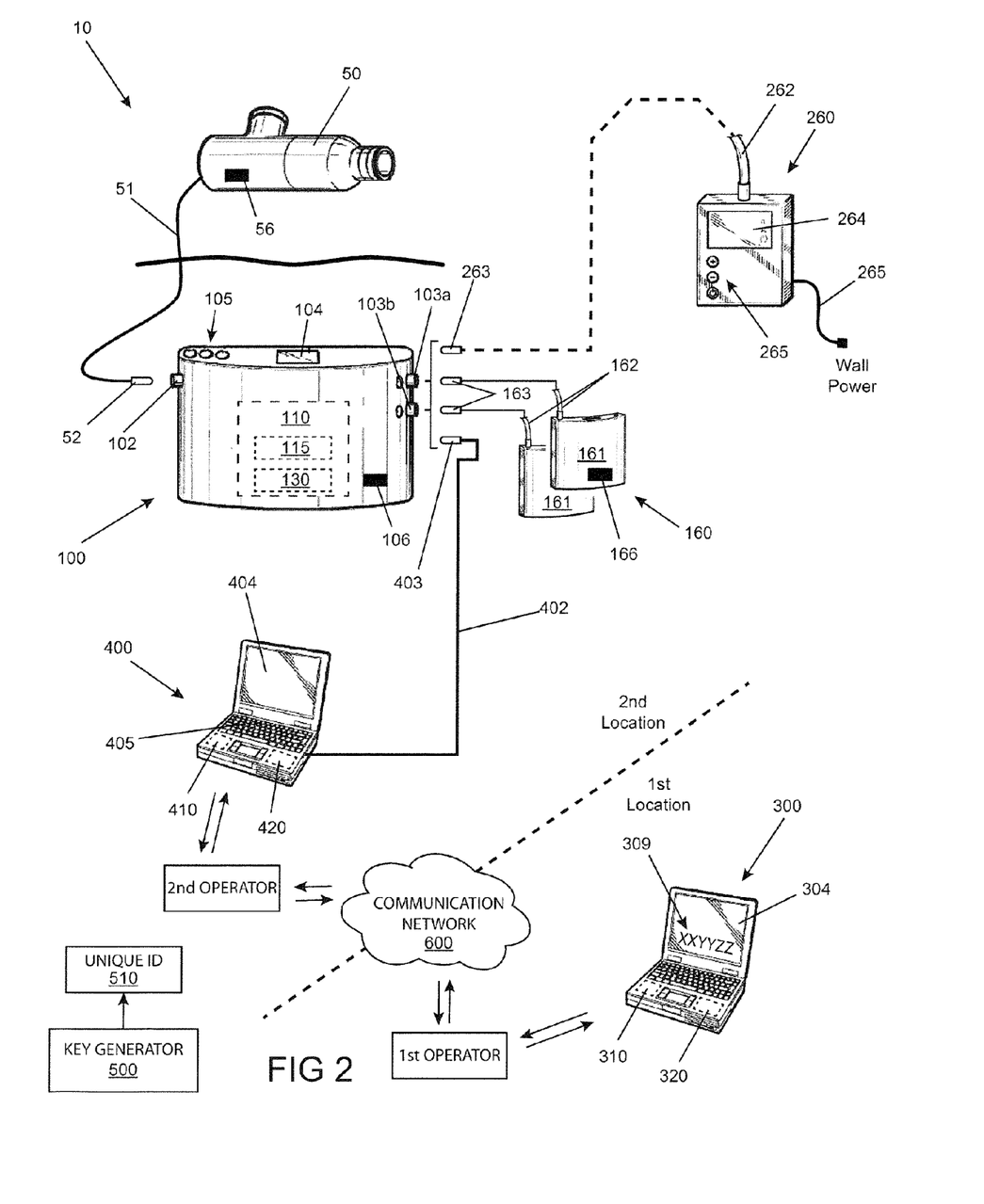
FIG. 2 is a schematic view of a fluid flow system including one or more components configured to communicate via a communication network and at least one human operator, consistent with the present inventive concepts

Referring now to FIG. 2, a schematic view of a fluid flow system for a patient is illustrated, including one or more components configured to communicate via a communication network and at least one human operator, consistent with the present inventive concepts. Components of system 10 can be configured similar to those of system 10 of FIG. 1. In the embodiment shown, local communication device 400 comprises a conduit 402 and connector 403, configured to operably connect local communication device 400 to controller 100. In the embodiment of FIG. 2, communication device 400 is configured to download pump operational parameters to controller 100 without the need for programmer 260' of FIG. 1. Connector 403 can comprise a connecting element selected from the group consisting of: an electrical connector; an optical connector; and combinations of these. In some embodiments, transceiver 420 can be configured to wirelessly transmit pump operational parameters to processor 110, such as via transceiver 130 of controller 100. In some embodiments, local communication device 400 can comprise a second wireless transceiver, such as a Bluetooth transceiver, configured to wirelessly transmit pump operational parameters to processor 110, such as via transceiver 130. Local communication device 400 can further comprise display 404 and user input 405. User input 405 can comprise a keyboard, pointing device such as a mouse, and/or a voice recognition module.

Also in the embodiment shown, the remote communication device 300 is configured to communicate with the local communication device 400 via a communication network, communication network 600, including at least one a human operator to enable communication between the devices 300 and 400. This communication can be achieved over a voice network with a first operator at a first location (e.g. a clinician or caregiver at a clinical location) and a second operator at a second location (e.g. a patient or caregiver at the patient location). In some embodiments, a command 309 is presented on a display 304 of remote communication device 300. The command comprises an encrypted command including a sequence of characters. The first operator verbalizes command 309 to a second operator. The second operator inputs the command into local communication device 400 via user input 405. In alternate embodiments, remote communication device 300 can deliver command 309 to the second user without the interaction of the first user, such as by a voice generator configured to dictate commands, or via email or other non-verbal communication. Similarly, the second operator inputs the voice generator presented command into local communication device 400 via user input 405. Authorized, acceptable commands, such as the valid commands described in reference to decode 410 of FIG. 3B herebelow, are transferred from local communication device 400 to controller 100 for further processing.

Figure 3A:
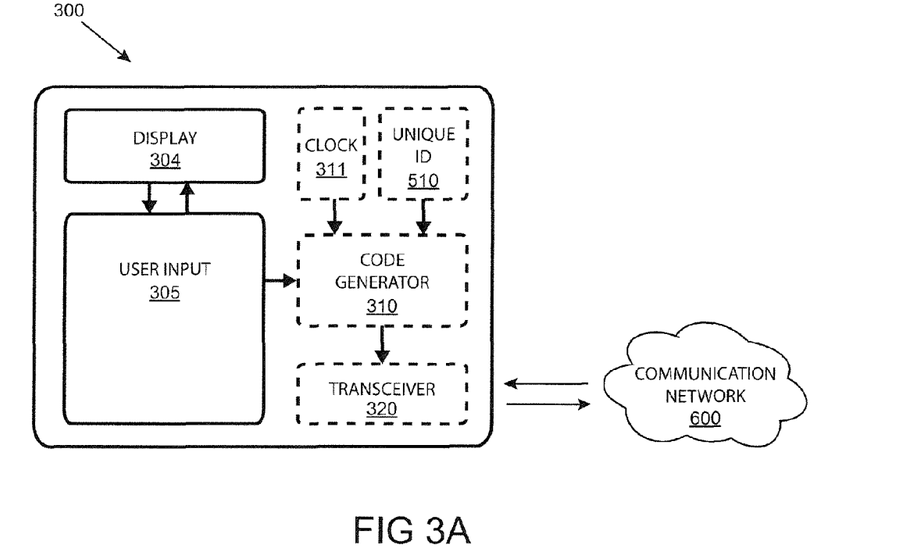
FIG. 3A is a schematic view of a remote communication device, configured to be positioned at a location remote from a patient, consistent with the present inventive concepts
Figure 3B:
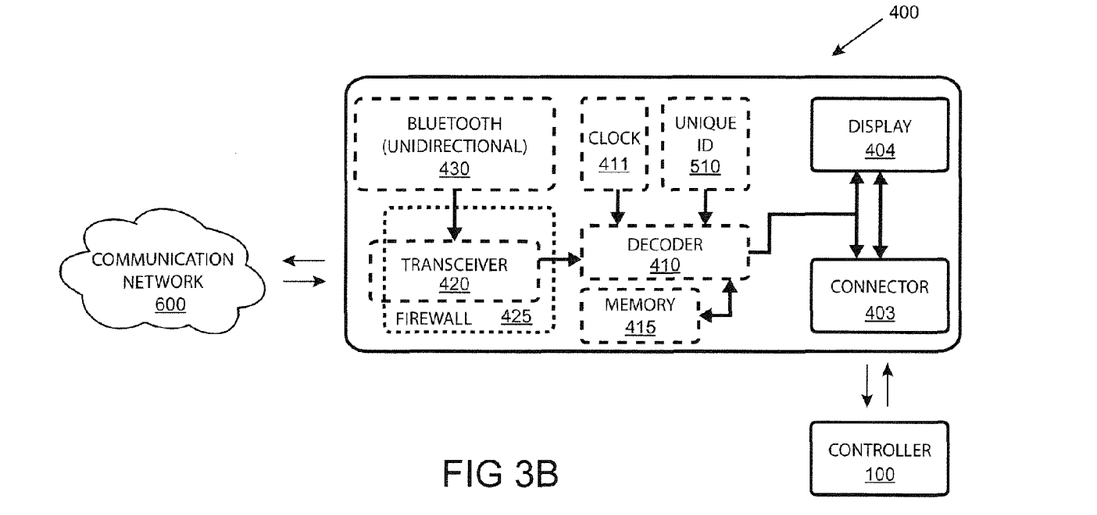
FIG. 3B is a schematic view of a local communication device, configured to be positioned at a patient location, consistent with the present inventive concepts.

Referring now to FIGS. 3A and 3B, schematic views of first and local communication devices are shown, consistent with the present inventive concepts. In FIG. 3A, remote communication device 300 is shown with high level schematic components illustrated. Remote communication device 300 comprises display 304 and user input 305, configured to allow a first user (e.g. a physician) to set or modify one or more pump operational parameters. Changes to pump operational parameters can include changes to parameters selected from the group consisting of: pump flow rate; pump maximum flow rate; pump minimum flow rate; pump fluid drive element speed; pump maximum fluid drive element speed; pump minimum fluid drive element speed; speed alternations and/or waveforms; alarm status; alarm level; alarm sensitivity; alarm type; temperature level; battery status; and combinations of these.

Remote communication device 300 includes unique ID 510, as well as a system clock 311. Unique ID 510 can be stored in a read protected memory module, such that unique ID 510 can be used to generate encrypted commands, but cannot be read or modified by an unauthorized user or program. System clock 311 can provide temporal information selected from the group consisting of: time of day information; date information; and combinations of these. Remote communication device 300 includes an encryption module, code generator 310, configured to generate encrypted commands based on at least one of: user defined changes to pump operational parameters; temporal data from clock 311; or unique ID 510. These factors can be used to generate an encrypted command using a cryptographic hash function performed by code generator 310. In some embodiments, code generator 310 is configured to produce a first encrypted command based on the user defined changes to the pump operational parameters and unique ID 510. In these embodiments, code generator 310 can be further configured to produce a first encrypted command also using clock 311 data. Code generator 310 can be configured to produce a first encrypted command including at least one verification bit, such as when the at least one verification bit comprises a checksum.

Remote communication device 300 further includes a communication module, transceiver 320. Transceiver 320 is configured to send encrypted commands over a communication network, such as communication network 600, to local communication device 400. Communication network 600 can comprise a network selected from the group consisting of: the internet; cellular service; satellite communication; fiber optic network; phone line; and combinations of these. In FIG. 3B, local communication device 400 is shown with high level schematic components illustrated. Local communication device 400 comprises a communication module, transceiver 420, including a firewall 425. Transceiver 420 is configured to receive encrypted commands over communication network 600 from remote communication device 300.

Local communication device 400 includes unique ID 510, as well as a system clock 411. Unique ID 510 can be stored in a read protected memory module, such that the unique ID can be used to decode encrypted commands, but cannot be read or modified by an unauthorized user or program. System clock 411 can provide temporal information selected from the group consisting of: time of day information; date information; and combinations of these. Local communication device 400 includes a decryption module, decoder 410, configured to decode incoming messages received by transceiver 420, based on at least one of temporal data from clock 411 or unique ID 510. A message can be a stream of incoming data, received by transceiver 420. A message is perceived as a valid command after decoder 410 has confirmed its validity, as described herebelow. Firewall 425 can be configured to prevent access to decoder 410 via communication network 600, such as to prevent unauthorized access or otherwise harmful communication between communication network 600 and decoder 410. Firewall 425 isolates transceiver 420 from one or more components of local communication device 400, such that only valid commands can pass through to subsequent electronic modules (i.e. all incoming messages must pass through decoder 410 and be verified or rejected). In some embodiments, local communication device 400 can be configured to alert the user if an incoming message (e.g. a message including an attempted command) is determined to be invalid, as is described in reference to decoder 410 herebelow. In some embodiments, an alert state can be increased (e.g. a more urgent alert state is activated) if multiple invalid messages are received within a certain, pre-determined time period, or if a limit of invalid messages received over a longer time period is reached (e.g. an amount of invalid messages above a threshold).

Decoder 410 is constructed and arranged to decode messages received by transceiver 420, confirm the message received is a valid command sent from remote communication device 300, and determine the intended changes to pump operational parameters encoded within the command. If a message is determined to be a valid command, these intended changes are then downloaded to controller 100, such as via connector 403, such that processor 110 generates a modified control signal to operate pump 50, as described in reference to FIG. 1 hereabove. In some embodiments, decoder 410 of local communication device 400 can decode the received message using unique ID 510, such that only a message containing a command which has been encrypted using matching unique ID 510 (i.e. unique ID 510 of remote communication device 300) will be determined to be a valid command. A message can be determined to be invalid if the incorrect unique ID was used during encryption and/or if the received code is not encrypted, such that the decryption algorithm will generate an invalid output. A message can also be determined to be invalid if a verification bit and/or a checksum is missing or invalid. A message can also be determined to be invalid if the correct unique ID was used during encryption, but the command has expired, such as when the time data included in the command is outside of an acceptable parameter (i.e. too much time has passed since the command was encrypted). In some embodiments, local communication device 400 can include a memory module 415 configured to store previous messages containing valid commands received from remote communication device 300. Local communication device 400 can be configured to compare incoming messages containing valid commands to previous messages such as to ensure that a command in not unintentionally repeated (e.g. no two encrypted messages will ever be identical, such that a repeated command will result in a unique encrypted message, which can never be repeated).

If the encrypted command is not valid (e.g. was not encrypted using the proper unique ID), local communication device 400 will not transmit the pump operational parameter change information to processor 110 as described hereabove. In some embodiments, local communication device 400 may display a warning, such as an error message displayed on display 404 signaling to the user that an invalid command was received. Local communication device 400 can also display a confirmation message, such as when a valid command is decoded and/or successfully transferred to controller 100. Display 404 can comprise an indicator selected from the group consisting of: light emitting element; vibrational transducer; audio transducer; alphanumeric display; and combinations of these.

Local communication device 400 can comprise an unidirectional transceiver, Bluetooth module 430, configured to receive diagnostic data from pump 50 and/or controller 100. Bluetooth module 430 can be configured as a unidirectional transceiver such that data can be received, and no information can be sent to controller 100 and/or pump 50, such as to ensure the integrity of operation of pump 50 as described herein. Bluetooth module 430 can receive information, such as information gathered from one or more sensors of system 10, including information selected from the group consisting of: pump rotational speed; pump housing temperature; blood temperature in pump; flow rate through pump; blood pressure; $SpO_2$ levels; other physiological parameters; battery status; and combinations of these. Data received by Bluetooth module 430 can be transmitted through transceiver 420 to remote communication device 300 via communication network 600.

Figure 4:
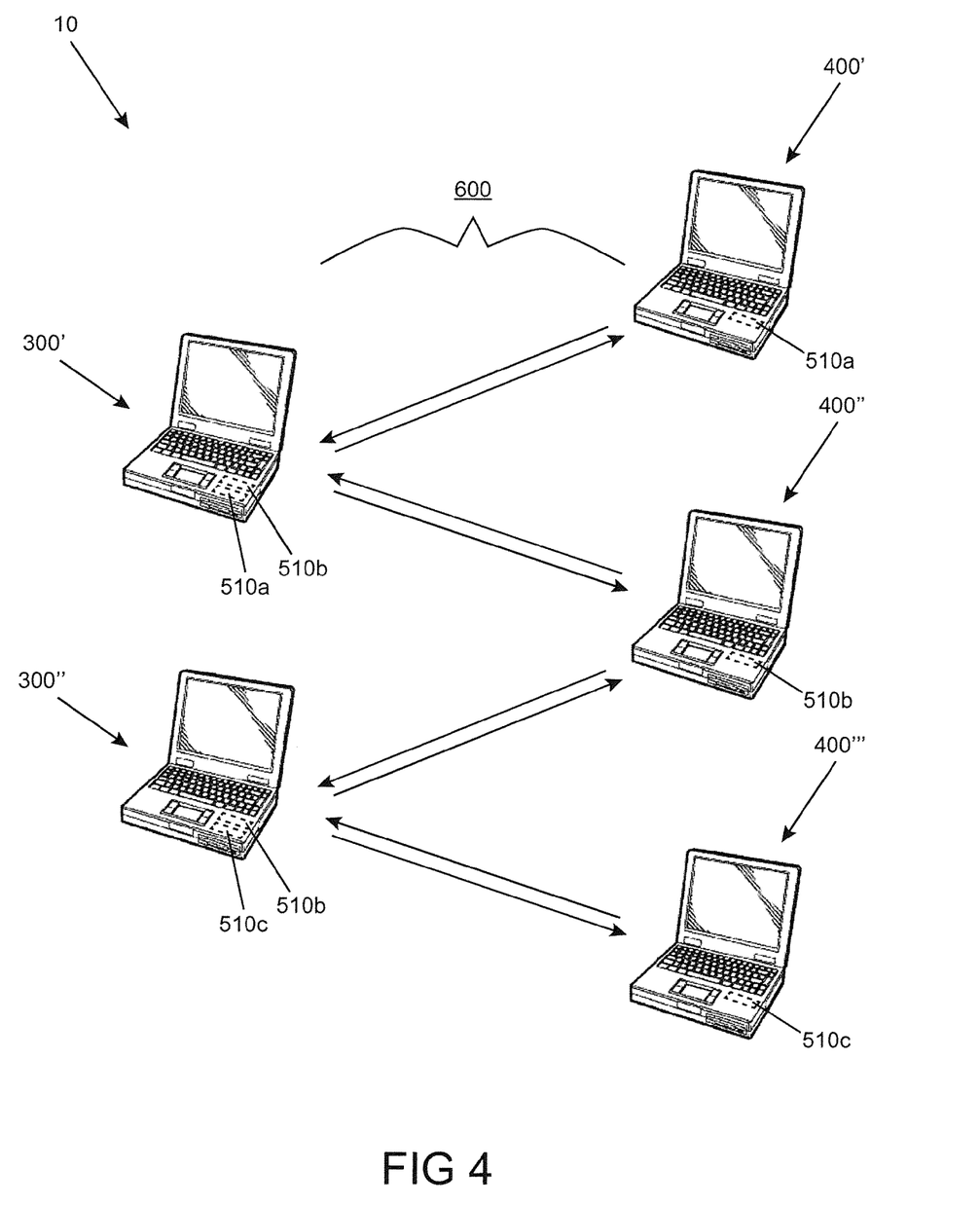
FIG. 4 is a schematic view of a set of local and remote communication devices of a fluid flow system, consistent with the present inventive concepts.

Referring now to FIG. 4, a schematic view of a set of local and remote communication devices of a fluid flow system is illustrated, consistent with the present inventive concepts. System 10 includes multiple remote communication devices, 300' and 300", and multiple local communication devices 400', 400" and 400''', each configured to communicate via communication network(s) 600. Each local communication device 400', 400" and 400''' is accompanied with a programmer 260, a controller 100 and a pump 50 not shown for illustrative clarity but typically configured as described herein in reference to FIG. 1 hereabove and in the local environment of a patient implanted with pump 50. Remote communication devices 300' and 300" can be located at a healthcare provider site such as a first clinician office, a second clinician office or a hospital.

Local communication device 400' includes unique identifier 510a. Local communication device 400" includes unique identifier 510b. Location communication device 400''' includes unique identifier 510c. Unique identifiers 510a-c can be generated and configured as described in reference to unique identifier 510 of FIG. 1.

Remote communication device 300' includes unique identifier 510a such that remote communication device can send encrypted commands as described herein to local communication device 400'. A command encrypted and otherwise generated by remote communication device 300' using unique identifier 510a can be created to remotely modify one or more pump operational parameters of the pump 50 co-located with local communication device 400' in a secure fashion (e.g. to prevent unauthorized changes). Remote communication device 300' further includes a second unique identifier, unique identifier 510b, such that remote communication device 300' can similarly, securely communicate with local communication device 400", such as to remotely modify one or more pump operational parameters of the pump 50 co-located with local communication device 400". Remote communication device 300" also includes unique identifier 510b, such that remote communication device 300" can also securely communicate with local communication device 400", such as when remote communication device 300' is at a first clinician's office and second communication device 300" is at a second clinician's office or in a hospital or other clinical setting. Remote communication device 300" further includes unique identifier 510c, such that remote communication device 300" can securely communicate with local communications device 400''' such as to modify one or more pump operational parameters of the pump 50 co-located with local communication device 400'''.

System 10 can include numerous configurations of one or more local communication devices 400 (including the associated pump 50 and other system components described in reference to FIG. 1 hereabove) and one or more remote communication devices 300. Each communication device 300 or 400 may include one or more unique identifiers such as to provide secure communication and modification of one or more pump operational parameters. Each remote communication device 300 can include one or more unique identifiers, such as one or more unique identifiers stored in a lookup table of memory, such as a lookup table associated with a list of patients. In some embodiments, one or more local communication devices 400 comprises multiple unique identifiers, such as multiple unique identifiers used to secure communication of a local communication device 300 with multiple remote communication devices containing different unique identifiers. Each unique identifier can be produced by a security key generator, such as security key generator 500 of FIG. 1.

While the preferred embodiments of the devices and methods have been described in reference to the environment in which they were developed, they are merely illustrative of the principles of the inventions. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it can be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A blood flow system for a patient comprising:
   a controller comprising:
      a processing unit comprising a signal generator and one or more blood pump operational parameters, wherein the signal generator is constructed and arranged to deliver a drive signal; and
      a battery constructed and arranged to provide power to the processing unit;
   an implantable blood pump assembly constructed and arranged to receive the drive signal from the processing unit and propel blood based on the drive signal;
   a security key generator constructed and arranged to produce a unique identifier;
   a remote communication device comprising a code generator and the unique identifier produced by the security key generator, wherein the code generator is constructed and arranged to produce encrypted commands based on the unique identifier; and
   a local communication device comprising the unique identifier; wherein the local communication device is constructed and arranged to receive the encrypted commands from the remote communication device, decrypt the encrypted commands using the unique identifier, and modify a blood pump operational parameter of the processing unit based on the decrypted commands.

2. The system of claim 1 wherein the processing unit is constructed and arranged to deliver the drive signal to the implantable blood pump assembly based on the one or more pump operational parameters.

3. The system of claim 1 further comprising a programmer including a first connector, wherein the processing unit includes a second connector constructed and arranged to operably connect to the first connector, wherein the programmer communicates with the processing unit via the first connector.

4. The system of claim 3 wherein the programmer is constructed and arranged to be maintained at a location remote from the patient.

5. The system of claim 3 wherein the programmer is constructed and arranged to modify at least one blood pump operational parameter of the processing unit.

6. The system of claim 5 wherein the programmer is constructed and arranged to prevent the patient from changing the at least one blood pump operational parameter.

7. The system of claim 3 wherein the programmer is constructed and arranged to transfer power to the controller.

8. The system of claim 1 wherein the processing unit comprises a wireless transmitter.

9. The system of claim 1 wherein the one or more blood pump operational parameters comprise a parameter selected from the group consisting of: blood pump flow rate; blood pump maximum flow rate; blood pump minimum flow rate; blood pump fluid drive element speed; blood pump maximum fluid drive element speed; blood pump minimum fluid drive element speed; speed alternations and/or waveforms; alarm status; alarm level; alarm sensitivity; alarm type; temperature level; battery status; and combinations thereof.

10. The system of claim 1 wherein the processing unit comprises an alarm algorithm, and the one or more blood pump operational parameters comprise an alarm algorithm parameter.

11. The system of claim 1 wherein the security key generator is further constructed and arranged to produce a second unique identifier for a second blood flow system.

12. The system of claim 1 further comprising a second local communication device and wherein the security key generator is further constructed and arranged to produce a second unique identifier for the second local communication device.

13. The system of claim 1 further comprising a second remote communication device and wherein the security key generator is further constructed and arranged to produce a second unique identifier for the second remote communication device.

14. The system of claim 1 wherein the code generator is constructed and arranged to produce a first encrypted command by encrypting blood pump operational parameter change information with the unique identifier.

15. The system of claim 14 wherein the remote communication device comprises a user interface constructed and arranged to allow an operator to input the blood pump operational parameter change information.

16. The system of claim 14 wherein the first encrypted command comprises a command received by the local communication device.

17. The system of claim 16 wherein the local communication device is constructed and arranged to decrypt the first encrypted command and transmit the blood pump operational parameter change information to the processing unit if the first encrypted command is based on a proper unique identifier.

18. The system of claim 16 wherein the local communication device is constructed and arranged to decrypt the first encrypted command and not transmit the blood pump operational parameter change information to the processing unit if the first encrypted command is not based on a proper unique identifier.

19. The system of claim 1 wherein the local communication device comprises a first local communication device, wherein the system further comprises a second local communication device comprising a second unique identifier produced by the security key generator, wherein the remote communication device further comprises the second unique identifier, and wherein the remote communication device is constructed and arranged to communicate with the first local communication device and the second local communication device.

20. The system of claim 19 wherein the remote communication device comprises a lookup table comprising the first unique identifier and the second unique identifier.

21. The system of claim 1 wherein the local communication device further comprises a user interface constructed and arranged to receive the encrypted commands from a first human operator.

22. The system of claim 1 wherein the local communication device is constructed and arranged to receive a message and to alert a user if the message is determined to be invalid.

23. The system of claim 22 wherein the local communication device is constructed and arranged to enter an alarm state if multiple invalid messages are received.

24. The system of claim 23 wherein the local communication device is constructed and arranged to enter alarm state if the multiple invalid messages are received within a pre-determined time period.

25. The system of claim 1 wherein the remote communication device comprises a first remote communication device, wherein the system further comprises a second remote communication device comprising a second unique identifier produced by the security key generator, wherein the local communication device further comprises the second unique identifier, and wherein the local communication device is constructed and arranged to communicate with the first remote communication device and the second remote communication device.

26. The system of claim 25 wherein the local communication device comprises a lookup table comprising the first unique identifier and the second unique identifier.

27. The system of claim 1 further comprising an error correction algorithm constructed and arranged to correct errors in communication between the local communication device and the remote communication device.

28. A method of modifying an operational parameter of a blood flow system comprising:
providing a blood flow system comprising:
a controller comprising:
a processing unit comprising a signal generator and one or more blood pump operational parameters, wherein the signal generator is constructed and arranged to deliver a drive signal; and
a battery constructed and arranged to provide power to the processing unit;
an implantable blood pump assembly constructed and arranged to receive the drive signal from the processing unit and propel blood based on the drive signal;
a security key generator constructed and arranged to produce a unique identifier;
a remote communication device comprising the unique identifier produced by the security key generator and a code generator, wherein the code generator is constructed and arranged to produce encrypted commands based on the unique identifier; and
a local communication device comprising the unique identifier; wherein the local communication device is constructed and arranged to receive the encrypted commands from the remote communication device and modify a blood pump operational parameter of the processing unit based on the received encrypted command;
having the security key generator produce the unique identifier;
incorporating the unique identifier into the remote communication device and the local communication device;
generating an encrypted command with the remote communication device that includes a proposed modification to one or more blood pump operational parameters;
receiving the encrypted command with the local communication device and confirming the acceptability of the encrypted command; and
modifying the one or more blood pump operational parameters of the processing unit if the encrypted command acceptability is confirmed.

29. The method according to claim 28 wherein modifying the one or more blood pump operational parameters modifies a blood pump alarm state.

30. The method according to claim 28 wherein modifying the one or more blood pump operational parameters modifies a blood pump flow rate.

* * * * *